United States Patent
Sambusseti

(10) Patent No.: US 9,949,819 B2
(45) Date of Patent: Apr. 24, 2018

(54) NON-ABSORBABLE TISSUE RECONSTRUCTION DEVICE, IN PARTICULAR FOR TISSUES SUCH AS LIGAMENTS

(71) Applicant: Antonio Sambusseti, Cremona (IT)

(72) Inventor: Antonio Sambusseti, Cremona (IT)

( * ) Notice: Subject to any disclaimer, the term of this patent is extended or adjusted under 35 U.S.C. 154(b) by 0 days.

(21) Appl. No.: 15/118,694

(22) PCT Filed: Feb. 12, 2015

(86) PCT No.: PCT/IB2015/051050
§ 371 (c)(1),
(2) Date: Aug. 12, 2016

(87) PCT Pub. No.: WO2015/121819
PCT Pub. Date: Aug. 20, 2015

(65) Prior Publication Data
US 2017/0049556 A1 Feb. 23, 2017

(30) Foreign Application Priority Data

Feb. 13, 2014 (IT) .............. MI2014A0206

(51) Int. Cl.
*A61F 2/08* (2006.01)
*A61B 17/11* (2006.01)

(52) U.S. Cl.
CPC ............ *A61F 2/08* (2013.01); *A61B 17/1146* (2013.01); *A61F 2210/0004* (2013.01); *A61F 2210/0076* (2013.01); *A61F 2250/0031* (2013.01); *A61F 2250/0059* (2013.01)

(58) Field of Classification Search
CPC ........ A61F 2/08; A61F 2/0805; A61F 2/0811; A61F 2002/0864; A61F 2002/0894; A61F 2002/0817; A61F 2310/00161; A61F 2310/00574; A61B 17/1146
USPC ....................................... 623/13.14
See application file for complete search history.

(56) References Cited

U.S. PATENT DOCUMENTS

| | | | | | |
|---|---|---|---|---|---|
| 3,882,551 | A | * | 5/1975 | Helmer ...................... | A61F 2/08 128/DIG. 21 |
| 3,971,670 | A | * | 7/1976 | Homsy ...................... | A61F 2/08 156/196 |
| 3,973,277 | A | * | 8/1976 | Semple ...................... | A61F 2/08 623/13.14 |
| 4,149,277 | A | * | 4/1979 | Bokros ...................... | A61F 2/08 623/13.2 |
| 4,187,558 | A | * | 2/1980 | Dahlen ...................... | A61F 2/08 623/13.14 |
| 4,246,660 | A | * | 1/1981 | Wevers ...................... | A61F 2/08 403/111 |

(Continued)

*Primary Examiner* — Alvin Stewart
(74) *Attorney, Agent, or Firm* — Abelman, Frayne & Schwab

(57) ABSTRACT

There is described a device (1) of the reversible type for the connection and reconstruction of a ligament, comprising a central reconstruction portion (9) and two connecting portions (10a, 10b) at the two ends of said central portion (9), characterized in that said connection device is made of silicone, said central portion covers said two connecting portions (10a, 10b), said two connecting portions (10a, 10b) being generally grid-shaped for receiving fixing means adapted to fix said device (1) to said ligament, said device (1) further comprising an outer carbon coating (14).

8 Claims, 3 Drawing Sheets

(56) References Cited

U.S. PATENT DOCUMENTS

| | | | | |
|---|---|---|---|---|
| 4,329,743 A * | 5/1982 | Alexander | A61B 17/80 | 428/408 |
| 4,345,339 A * | 8/1982 | Muller | A61F 2/08 | 623/13.2 |
| 4,483,023 A * | 11/1984 | Hoffman, Jr. | A61F 2/08 | 623/13.15 |
| 4,610,688 A * | 9/1986 | Silvestrini | A61F 2/06 | 623/1.53 |
| 4,642,119 A * | 2/1987 | Shah | A61F 2/08 | 623/13.2 |
| 4,662,886 A * | 5/1987 | Moorse | A61B 17/06166 | 606/230 |
| 4,731,084 A * | 3/1988 | Dunn | A61F 2/08 | 623/13.19 |
| 4,834,755 A * | 5/1989 | Silvestrini | A61F 2/06 | 623/1.53 |
| 4,894,063 A * | 1/1990 | Nashef | A61F 2/08 | 623/13.17 |
| 4,917,700 A * | 4/1990 | Aikins | A61F 2/08 | 623/13.19 |
| 4,946,377 A * | 8/1990 | Kovach | A61F 2/08 | 623/13.18 |
| 5,176,708 A * | 1/1993 | Frey | A61F 2/08 | 623/13.2 |
| 5,217,495 A * | 6/1993 | Kaplan | A61F 2/06 | 57/225 |
| 5,290,271 A * | 3/1994 | Jernberg | A61F 2/06 | 424/473 |
| 5,376,118 A * | 12/1994 | Kaplan | A61F 2/06 | 606/228 |
| 5,458,636 A * | 10/1995 | Brancato | A61F 2/0063 | 606/151 |
| 5,514,181 A * | 5/1996 | Light | A61B 17/1146 | 606/229 |
| 5,549,676 A * | 8/1996 | Johnson | A61F 2/08 | 623/13.13 |
| 5,800,543 A * | 9/1998 | McLeod | A61F 2/08 | 623/13.19 |
| 6,203,572 B1 * | 3/2001 | Johnson | A61F 2/08 | 606/108 |
| 6,638,312 B2 * | 10/2003 | Plouhar | A61F 2/0063 | 623/23.72 |
| 2001/0044659 A1 * | 11/2001 | Laboureau | A61F 2/08 | 623/13.2 |
| 2002/0055749 A1 * | 5/2002 | Esnouf | A61F 2/08 | 606/148 |
| 2003/0078659 A1 * | 4/2003 | Yang | A61F 2/08 | 623/13.17 |
| 2004/0267362 A1 * | 12/2004 | Hwang | A61F 2/08 | 623/13.15 |
| 2005/0049702 A1 * | 3/2005 | Melvin | A61B 17/0401 | 623/11.11 |
| 2005/0192581 A1 * | 9/2005 | Molz | A61B 17/842 | 606/74 |
| 2007/0027542 A1 * | 2/2007 | Xu | A61F 2/08 | 623/13.17 |
| 2007/0118217 A1 * | 5/2007 | Brulez | A61F 2/08 | 623/13.2 |
| 2007/0123984 A1 * | 5/2007 | Hodorek | A61F 2/0811 | 623/13.14 |
| 2007/0150064 A1 * | 6/2007 | Ruberte | A61F 2/442 | 623/17.16 |
| 2008/0027542 A1 * | 1/2008 | McQuillan | A61L 27/3683 | 623/13.11 |
| 2009/0287308 A1 * | 11/2009 | Davis | A61F 2/08 | 623/13.12 |
| 2009/0306775 A1 | 12/2009 | Macossay-Torres | | |
| 2010/0161054 A1 * | 6/2010 | Park | A61L 27/48 | 623/13.14 |
| 2010/0298937 A1 * | 11/2010 | Laurencin | A61F 2/08 | 623/13.14 |
| 2011/0295284 A1 * | 12/2011 | Purdue | A61F 2/08 | 606/151 |
| 2012/0239145 A1 * | 9/2012 | Peterson | A61F 2/08 | 623/13.14 |
| 2014/0039620 A1 * | 2/2014 | Cantournet | A61F 2/08 | 623/13.14 |
| 2014/0172096 A1 * | 6/2014 | Koob | A61F 2/08 | 623/13.19 |
| 2014/0257349 A1 * | 9/2014 | Sudekum | A61F 2/0811 | 606/151 |
| 2014/0324078 A1 * | 10/2014 | Buschmann | A61L 27/18 | 606/151 |
| 2014/0371854 A1 * | 12/2014 | Engin | A61F 2/08 | 623/14.13 |
| 2017/0079769 A1 * | 3/2017 | Greenhalgh | A61F 2/08 | |

* cited by examiner

NON-ABSORBABLE TISSUE RECONSTRUCTION DEVICE, IN PARTICULAR FOR TISSUES SUCH AS LIGAMENTS

CROSS REFERENCE TO RELATED APPLICATIONS

This application is a national phase of PCT application No. PCT/IB2015/051050, filed Feb. 12, 2015, which claims priority to IT patent application No. MI2014A000206, filed Feb. 13, 2014, all of which are incorporated herein by reference thereto.

BACKGROUND ART

Ligaments are formations of fibrous connective tissue and combine two or more anatomical structures. The cruciate ligaments of the knee joint are fibrous bundles crossed with one another to support the joint itself and allow its joint movements. Many individuals—in particular those who practice a sport—undergo damage to these ligaments. These ligaments are not the only ones to get damaged, however they are the most frequent and most critical ones as regards their recovery process.

In order to reconstruct the tendons damaged upon a lesion there exists a technique known as "autologous". According to this surgical technique, a fiber bundle is used, which is taken from the ligaments which are used as a basis to reconstruct the damaged ligament. This technique is very invasive and cannot be always applied.

In response to the "autologous" technique, devices have been developed to "simulate" a ligament. Such devices have the shape and size of the ligament to be replaced and are made of polyester. At the ends thereof, there are fixing means (staples, anchors or absorbable or non-absorbable synthesis screws) to stably fix the artificial ligament and allow the partial reconstruction of the ligament tissue thereon. The implant of artificial ligaments of this type is final, over time a part of ligament reconstructs thereon and integrates its functions. Such devices ensure a good biocompatibility, however they have some drawbacks related to their mechanical function. In fact, their flexibility is acceptable but not excellent. Therefore, the performance of such devices is valid even if with some drawbacks, especially as regards the mechanical functionality. However, such a drawback can be especially insidious because such devices can be damaged even shortly after their installation, thus requiring a new operation to replace the device.

These drawbacks caused the "autologous" technique to be the predominant choice despite its limitations.

SUMMARY

Therefore, the known techniques described do not allow to have a device for the connection and reconstruction of torn ligaments.

This situation is particularly disadvantageous both for patients who suffer from such injuries and for the practitioners who apply non-optimal solutions to the problem in place, which often requires later corrective interventions or cause further damage to the patient.

It is the general object of the present invention to implement a device of the reversible type for the connection and reconstruction of a ligament, which allows the problems of the prior art to be solved in a simple and cost-effective manner.

It is the first specific object of the present invention to implement a device of the reversible type for the connection and reconstruction of a ligament, which is applicable irrespective of the physiological conditions of the individual to whom it is intended.

In general, a device of the reversible type for the connection and reconstruction of a ligament comprises a central reconstruction portion and two connecting portions at the two ends of said central portion, characterized in that said connection device is made of silicone, said central portion covers said two connecting portions, said two connecting portions being generally grid shaped for receiving fixing means adapted to fix said device to said ligament, said device further comprising an outer carbon coating.

Further advantageous technical features of the device according to the present invention are described in the dependent claims.

LIST OF FIGURES

The technical features of the present invention as well as advantages thereof will become apparent from the following description to be considered in conjunction with the accompanying drawings, in which.

DETAILED DESCRIPTION

The following description and the accompanying drawings are intended for illustrative purposes and therefore they do not limit the present invention, which may be implemented according to other and different embodiments; moreover, it is worth noting that these figures are diagrammatic and simplified.

Figure 1:
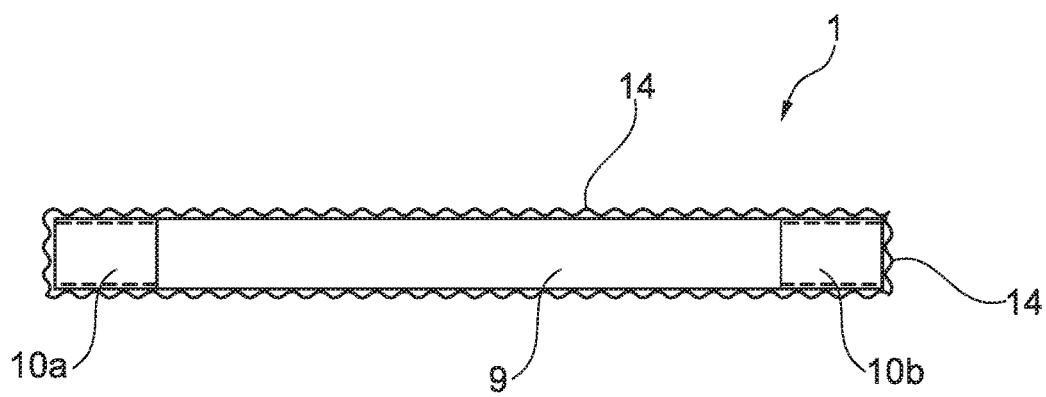
FIG. 1 shows a top view of a tissue reconstruction device according to the present invention.

With reference to FIG. 1, there is shown a device of the reversible type for the connection and reconstruction of ligaments according to the present invention. The term "reversible" means a device to be installed at a damaged ligament to allow the physiological tissue reconstruction thereof. Such a device is removed once the reconstruction has been completed, after a predetermined period of time. Such a device can be applied to a single ligament (e.g. the anterior cruciate ligament of the knee joint) or to a group of ligaments (e.g. the rotator cuff of the shoulder). Device 1 comprises a central reconstruction portion 9 and two connecting portions 10a, 10b at the two ends of the central portion 9. According to the present invention, the central reconstruction portion 9 is made of silicone and the connecting portions 10a, 10b are generally grid-shaped to receive fixing means adapted to fix said device to said ligaments. The central portion covers the connecting portions 10a and 10b. The device (i.e. the central portion 9 and the portions 10a and 10b) has an outer carbon coating 14.

It is worth noting that the connecting portions 10a and 10b have a general stiffness in order to receive the fixing means. Thereby, the two opposite end stretches of device 1 are configured to receive said fixing means, known per se, which comprise either absorbable or non-absorbable staples, anchors or synthesis screws.

The central portion 9 is a part of device 1 on which the tissue reconstruction for which the device 1 itself is intended takes place.

In use, the device is placed in a predetermined reconstruction position according to anatomical constraints and to the extent of the ligament portion to be reconstructed. It is therefore essential, for a successful reconstruction of the ligament, that the device remains in such a position for the entire duration of the reconstruction process. To this end, the two connecting portions 10a, 10b are configured to receive the fixing means stably after the operations aimed to place it in its reconstruction position. In this first condition, the device has such a structure as to favor the tissue regrowth.

Thereafter, the physiological reconstruction process absorbs the fixing means; the ligament (or ligaments, in the case of a bundle of ligaments for which a device according to the present invention is to be used) under reconstruction has its tissue regrowth on the central portion 9 of the device. In this second condition, the device has such a structure as to support the tissue regrowth, and in particular up to its complete reconstruction.

The ends 10a and 10b are not reabsorbed with the fixing means, they remain segregated from the central portion 9. Thereby, once the reconstruction has been completed, device 1 can be easily removed.

In particular, in the second condition, and in particular once the ligament reconstruction has been completed, the central portion 9 is completely or almost completely covered by fibers that make up the ligament. At this point, device 1 may be removed. According to an embodiment, the central portion 9 and the ends 10a and 10b are made of silicone and polyethylene terephthalate (e.g. using Dacron®), respectively. The central portion 9 covers the ends 10 and 10b and further comprises a carbon coating 14. The fibers that make up the ligament will advantageously reconstruct around the central portion 9 without settling thereon. Such a feature is achieved due to the carbon coating 14 which covers device 1. Therefore, the removal of the central portion 9 can take place with ease and especially without causing damage to the reconstructed ligament.

According to a preferred embodiment, the connecting portions 10a, 10b are made of polyethylene terephthalate.

Figure 2:
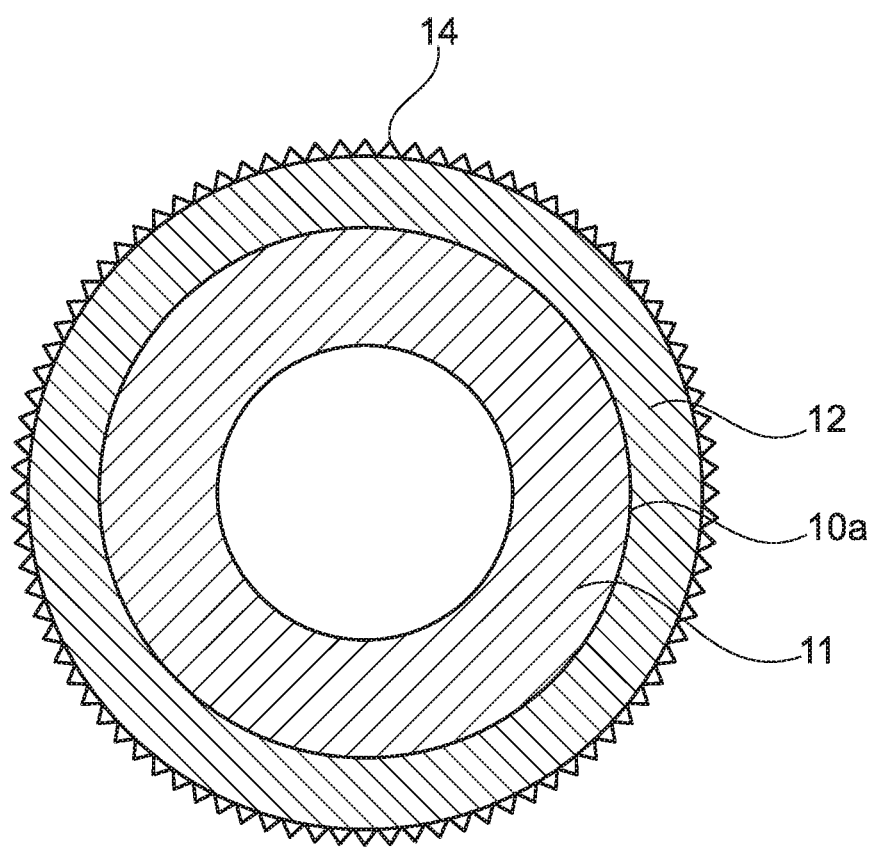
FIG. 2 shows a sectional view of a second embodiment of a tissue device according to the present invention.
Figure 3:
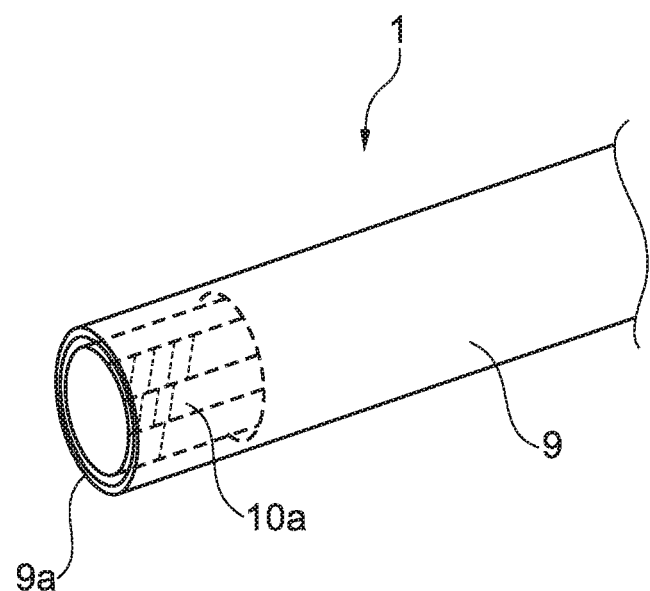
FIG. 3 shows a first embodiment of a tissue reconstruction device according to the present invention.

As seen in FIG. 2, according to a preferred embodiment, the central portion 9 is made with a plurality of superimposed silicone layers 11, 12.

The connecting portions 10a, 10b are made integral with the central portion 9 by fixing them between the two layers 11 and 12 (or between two layers of three or more layers which make up the central portion 9) of the central portion 9.

This device configuration is particularly sturdy and can be used for groups of ligaments which are larger than an average ligament, such as the rotator cuff.

The outer carbon coating 14 advantageously provides a high degree of biocompatibility with the tissues which it contacts.

Preferably, the central portion 9 of a device according to the present invention is a circular-base prism. Of course, different shapes are suitable to implement the section of the central portion 9, they may be evaluated from time to time in the light of the structural constraints to be met.

As seen in FIG. 4, according to an embodiment, the central portion 9 is a hollow cylinder. However, according to an alternative embodiment, the central portion 9 is a solid cylinder.

The dimensions of the central portion 9 are devised to fit any size of ligaments for which the device is intended. Such a portion has a diameter from 1 to 15 mm; a length from 5 to 45 mm.

Moreover, the connecting portions 10a, 10b are fixed to the central portion, respectively, overlapping by at least 1.5 cm said central portion 9.

The invention claimed is:

1. A device for the connection and reconstruction of a ligament of the reversible type comprising a central portion for reconstruction and two connecting portions to the two ends of said central portion, said device further comprising an outer carbon coating, characterized in that said central portion of said connection device is made of silicone, said central portion covers said two connecting portions, said two connecting portions being generally shaped as a grid for receiving fixing means adapted to fix said device to said ligament, and in that said central portion is made with a plurality of superimposed silicone layers.

2. A device according to claim 1, wherein said connecting portions are made of polyethylene terephthalate.

3. A device according to claim 1, wherein said connecting portions are fixed to said central portion between two silicone layers.

4. A device according to claim 1, wherein said central portion is a circular-base prism.

5. A device according to claim 1, wherein said central portion is a hollow cylinder.

6. A device according to claim 1, wherein said central portion has a diameter in the range from 1 to 15 mm.

7. A device according to claim 1, wherein said central portion has a length in the range from 5 to 45 mm.

8. A device according to claim 1, wherein said connecting portions are fixed to said central portion, respectively, and wherein each of said connecting portions overlaps said central portion by at least 1.5 cm.

* * * * *